(12) United States Patent
Wei et al.

(10) Patent No.: US 8,285,017 B2
(45) Date of Patent: Oct. 9, 2012

(54) METHODS FOR INTERACTIVE LABELING OF TUBULAR STRUCTURES IN MEDICAL IMAGING

(75) Inventors: Guo-Qing Wei, Plainsboro, NJ (US); Cheng-Chung Liang, West Windsor, NJ (US); Feng Ma, Pennington, NJ (US); Li Fan, Belle Mead, NJ (US); Jian-Zhong Qian, Princeton Junction, NJ (US); Xiaolan Zeng, Princeton, NJ (US)

(73) Assignee: Edda Technology, Inc., Princeton Junction, NJ (US)

( * ) Notice: Subject to any disclaimer, the term of this patent is extended or adjusted under 35 U.S.C. 154(b) by 654 days.

(21) Appl. No.: 12/565,370

(22) Filed: Sep. 23, 2009

(65) Prior Publication Data

US 2010/0079455 A1 Apr. 1, 2010

Related U.S. Application Data

(60) Provisional application No. 61/099,417, filed on Sep. 23, 2008.

(51) Int. Cl.
*G06K 9/00* (2006.01)

(52) U.S. Cl. ...................................................... 382/128

(58) Field of Classification Search .................. 382/128, 382/131, 154; 345/179; 128/920, 922
See application file for complete search history.

(56) References Cited

U.S. PATENT DOCUMENTS

| | | |
|---|---|---|
| 2005/0018885 A1 | 1/2005 | Chen et al. ................... 382/128 |
| 2005/0162413 A1 | 7/2005 | Dresevic et al. .............. 345/179 |
| 2005/0187900 A1 | 8/2005 | LeTourneau ..................... 707/1 |
| 2008/0044072 A1 | 2/2008 | Kiraly et al. ................. 328/128 |
| 2008/0187197 A1 | 8/2008 | Slabaugh et al. ............. 382/128 |

OTHER PUBLICATIONS

International Search Report and Written Opinion of the International Searching Authority issued in International Patent Application No. PCT/US 09/58058, mailed Nov. 30, 2009.

*Primary Examiner* — Andrew W Johns
(74) *Attorney, Agent, or Firm* — SNR Denton US LLP

(57) ABSTRACT

System and method for labeling a tubular structure. A tubular structure is first displayed on a display screen. A representation of the tubular structure can be obtained. A user draws a curve on the display screen using an electronic pen that is associated with a label. Based on the user drawn curve, one or more segments of the tubular structure that corresponds to the drawn curve are identified based on the representation of the segmented tubular structure. The label is then assigned to such identified one or more segments of the tubular structure.

30 Claims, 15 Drawing Sheets

METHODS FOR INTERACTIVE LABELING OF TUBULAR STRUCTURES IN MEDICAL IMAGING

The present invention claims priority of Provisional Application No. 61/099,417 filed on Sep. 23, 2008, the contents of which are incorporated herein in their entirety.

BACKGROUND

1. Technical Field

The present teaching relates generally to method and system of medical imaging and systems incorporating the same. More specifically, the present teaching relates to method and system for 2D/3D data processing in medical imaging and systems incorporating the same.

2. Discussion of Technical Background

In medical imaging, patient data may be acquired in different modalities, such as Computerized Tomography (CT), X-ray, or Magnetic Resonance Imaging (MRI). In today's society, there is a high percentage of the population that suffers from vascular diseases or other related diseases. In diagnosing such diseases, precise recognition and annotation/labeling of proper tubular anatomical structures, such as vascular structures, or airways, play a very important role in making medical diagnosis decisions. Computerized analysis and quantification of vascular structures frequently involves segmentation of vascular structures from other surrounding imaging content, labeling such identified structures, and making accurate measurements of different labeled structures.

Due to noise often present in medical imaging, artifacts, such as partial volume effect in CT images, or imperfection of the segmentation approaches used to identify the vascular structures, the vascular structures segmented from medical images often contain errors. For example, in medical images, vascular structures often appear broken or seemingly contain loops. This makes it difficult to label different vessel structures correctly. In addition, different vascular systems may appear intersecting with each other in images. Such consequences of noisy images make it difficult for a computing device to fully automate the process of efficiently labeling vascular structures. Furthermore, although models for different vascular systems, e.g., an anatomical atlas of human vascular systems, are often available, for the same reason, correctly labeling different segmented vascular structures according to such pre-defined models is difficult.

In an attempt to improve, semi-automated approaches have been developed. For example, solutions exists in which one or more seed points may be manually placed on vessel branches which are then used to automatically label a vessel starting from the seeds. However, this type of approach is usually not reliable because a vessel branch may be incorrectly connected to other vessel branches or to another vascular system because the segmented vessel branches may not be correct due to presence of noise.

Therefore, an improved approach that allows reliable and efficient labeling of vascular structures in inherently noisy medical images is needed.

BRIEF DESCRIPTION OF THE DRAWINGS

The inventions claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

DETAILED DESCRIPTION

Figure 1A:
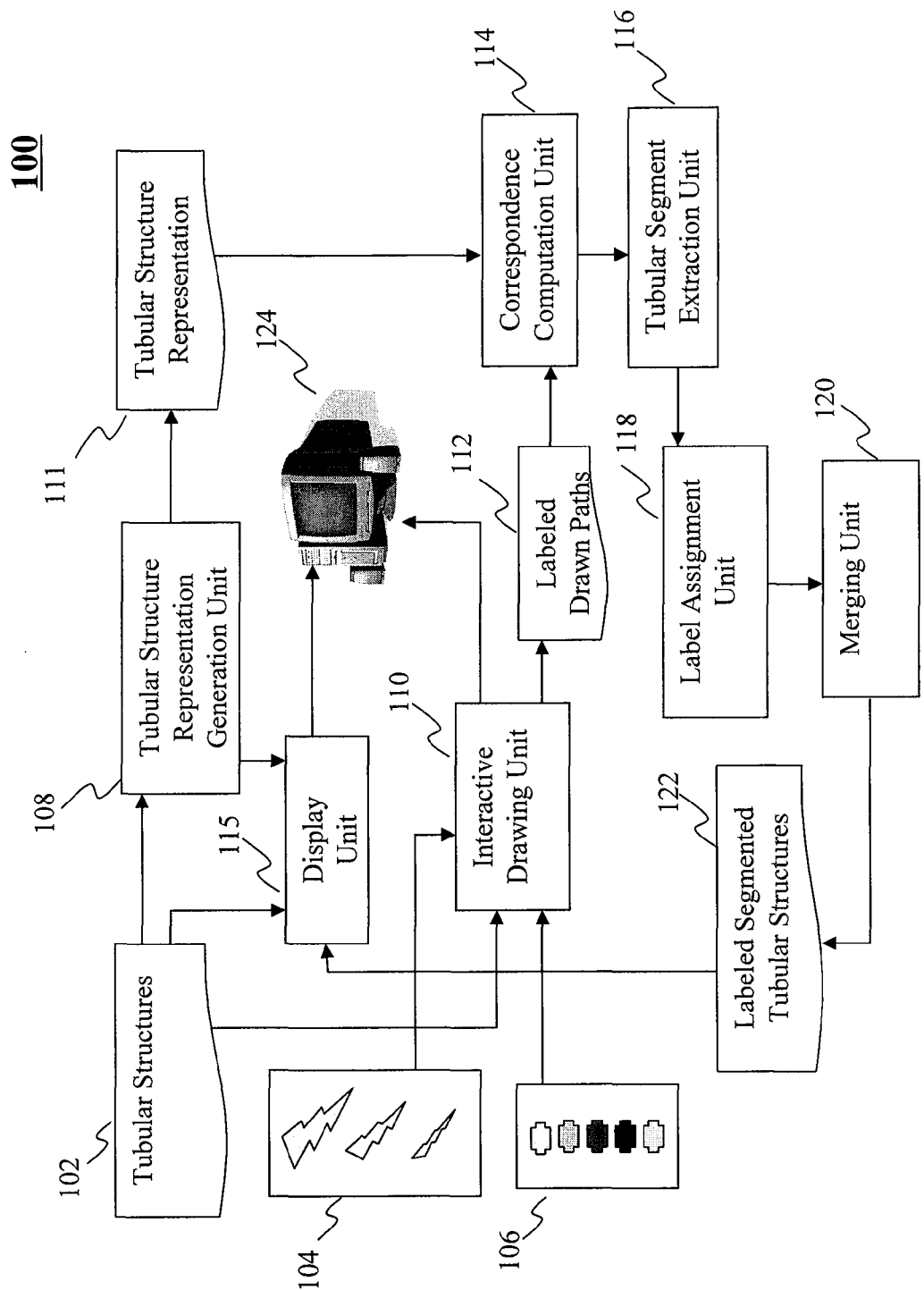
FIG. 1(a) depicts an exemplary diagram of a tubular structure labeling system, according to an embodiment of the present teaching.

The present teaching discloses interactive approaches to labeling tubular structures segmented from medical images. FIG. 1 depicts an exemplary diagram of a tubular structure labeling system 100, according to an embodiment of the present teaching. The exemplary system 100 includes a display screen 124 and a display unit 115 which is configured to display imagery data or any related information on the display screen 124. The system 100 also includes a tubular structure representation generation unit 108, which takes an image or volume with a tubular structure 102 as input and generates corresponding representations thereof, which are stored in storage 111. In some embodiments, the tubular structure 102 may be segmented. In this case, the representation is derived based on the segmentation result. In some embodiments, the tubular structure 102 corresponds to the original image or volume without segmentation. In this case, the tubular structure representation generation unit 108 may first perform a segmentation and then derive a representation based on the segmentation result. In some situations, the tubular structure representation generation unit 1088 may directly compute the representation of the tubular structure based on the original imagery data.

Additionally, the system 100 includes an interactive drawing unit 110, deployed to allow a user to draw a curve based on what is displayed on the display screen. A drawn curve can be made using an electronic pen, selected by the user from a collection of electronic pens (104) of various tip size, and with an associated label, also selected by the user from a collection of labels 106. For example, the user may draw a path (112) along an input tubular structures from 102 displayed on the display screen.

In operation, system 100 facilitates interaction with a user to retrieve some tubular structure from 102 and display it on the display screen. The input tubular structure can be either segmented or not segmented. A user may interact with the interactive drawing unit 110 to make a curve based on what is visible on the display screen. By such drawing operation, not only the curves are made but also the thickness of the curve is determined based on the user's selection of the pen's tip size. In addition, each selected pen is associated with a label so that the drawn curve is labeled in accordance with the label associated with the pen. Such generated drawn curves may be stored in storage 112.

System 100 comprises also a correspondence computing unit 114, designed for computing a correspondence between a structure representation of a tubular structure from storage 111 and a user-drawn path or curve from storage 112. Details related to the correspondence and the computation thereof are discussed herein with respect to FIGS. 3-4(*h*). Based on the correspondence computed, a tubular segment extraction unit 116 in system 100 extracts corresponding tubular segments in the underlying tubular structure. A label assignment unit 118 then assigns a label of the user-drawn path to all pixel/voxel points in such extracted tubular segment. In this way, the labeling of different tubular segments in a tubular structure can be achieved in an interactive manner with efficiency and improved accuracy.

As discussed herein, segmentation of tubular structure sometimes does not yield quality result. For instance, a continuous tubular branch may be segmented into different tubular segments. However, if a user-drawn path/curve does across different tubular segments, this can be used to improve the segmentation result by merging different tubular segments that all correspond to the same underlying user-drawn path. For that purpose, system 100 further includes a merging unit 120 deployed for merging broken segments of the tubular structure based on a user-drawn path. The merged tubular segment or structure is assigned with the same label. Such improved tubular segmentation result with assigned labels may then be stored in storage 122, which can be further retrieved by the display unit 115 to display on the display screen 124 to visualize the improved and labeled tubular structure.

FIG. 1(*b*) provides an example of a three dimensional segmented tubular structure which is rendered on a two dimensional display screen such as 124. As can be seen, such a tubular structure may have major trunks with different branches, some of which may have additional sub-branches. As discussed herein, different branches of the illustrated tubular structure may correspond to different anatomically identifiable parts and should be labeled differently. It can also be seen that labeling of such a three dimensional tubular structure can be quite challenging. The rest of this disclosure discusses how different steps may be carried out in accordance with the description herein to achieve more reliable and precise labeling of different portions of such a tubular structure.

FIG. 2(*a*) is a flowchart of an exemplary process of the tubular structure labeling system 100, according to an embodiment of the present teaching. A segmented tubular structure is first retrieved at 200, which is displayed, at 212, on the display screen 124. Input to the system are segmented tubular structures 210, that may be obtained by using any prior art segmentation methods. Depending on the image modality, a tubular structure may be two-dimensional (2D) or three-dimensional (3D). In 2D, a tubular structure may be represented by pixels, while in 3D it may be represented by voxels, which can be rendered in a 2D display screen. One such segmented tubular structure is shown in FIG. 1(*b*).

In some embodiments, a representation of the displayed tubular structure may then be computed at 214. In some embodiments, the representation may have been computed previously so that at step 214, the existing representation may be retrieved, at 214, from, e.g., the tubular structure representation storage 111. Such representation may correspond to a skeleton representation, as shown in FIG. 2(*b*), or any other form of representation for tubular structures known in the art. Such a skeleton representation is used in the subsequent steps to facilitate an improved tubular segment labeling operation as disclosed herein.

To start the interactive labeling process as disclosed herein, an interactive drawing session is, at 216, activated. During this interactive drawing session, a user first selects, at 218, an electronic pen with a desired pen tip size. The pen's tip size may be increased or decreased through an interface, e.g., a scrolling of middle mouse wheel. A label to be used to label desired tubular segments is also selected, at 220, to be associated with the selected pen. Such a label may be selected from a collection of labels defined according to some physiological models of a vascular system and made available to the system 100. For example, a label may correspond to a medical definition in human anatomy, e.g., second generation of middle hepatic vein of human liver organ. The set of labels are to be assigned to the branches of the tubular structure, according to some pre-defined criteria, e.g., an atlas of the human vascular system.

At step 222, the user uses the selected electronic drawing pen to draw a path along a tubular segment to be labeled. For 3D tubular structures, any 3D visualization method may be used to render the 3D tubular structures at, e.g., any user-selected angle that best visualizes a particular 3D segment. The width of the drawn path may be the same as the size of the electronic drawing pen tip. In some embodiments, once the user selects the thickness of the pen tip, the drawn curve may have the width consistent with the tip size. In some embodiments, while drawing the path, the user may be allowed to simultaneously adjust the tip size of the electronic drawing pen using, e.g., a middle mouse wheel.

In some embodiments, an automatic shape analysis may be performed with respect to the tubular segment(s) along which a drawn curve is made. Such shape analysis result, e.g., the width at any location of the tubular segment, may be used to automatically and dynamically adjust the size of the electronic drawing pen tip to match with the width of the tubular segment at the location of the pen tip. Such width of a tubular segment may be measured to be the diameter of each cross section of the tubular segment perpendicular to its longest principle axis.

Figure 2A:
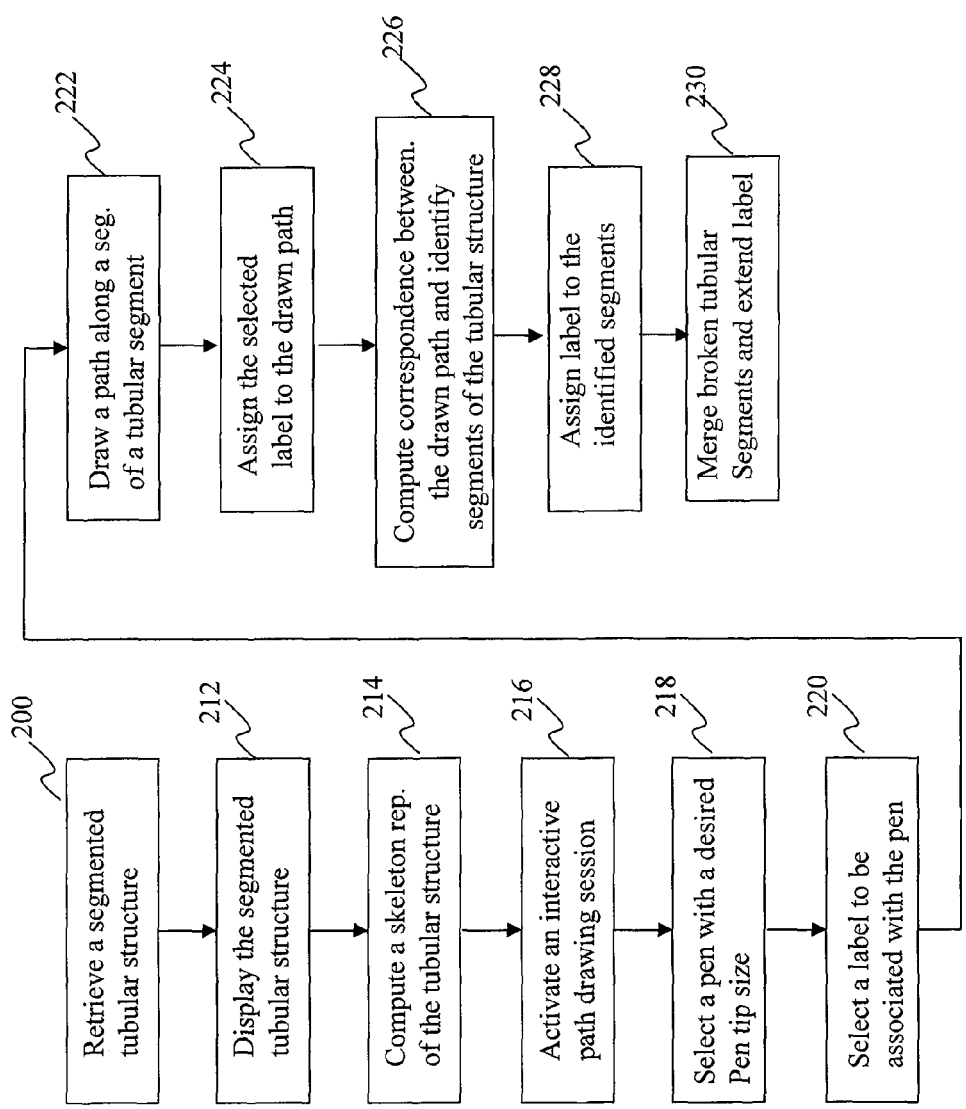
FIG. 2(a) depicts an exemplary flow diagram of a tubular structure labeling system, according to an embodiment of the present teaching.

The label associated with the selected pen may be automatically assigned, at 224, to the pixels points of the drawn path. The labeled path drawn with the selected pen having a selected or calculated tip size may be rendered or superimposed on top of the original tubular segment as displayed. This is illustrated in FIG. 2(c), where a small curve labeled as 230 corresponds to the drawn path by a user. The color of the drawn path encodes the label assigned to the path. The labeled drawn path is superimposed on a tubular structure and it corresponds, visually, to an underlying tubular segment 240.

Figure 2B:
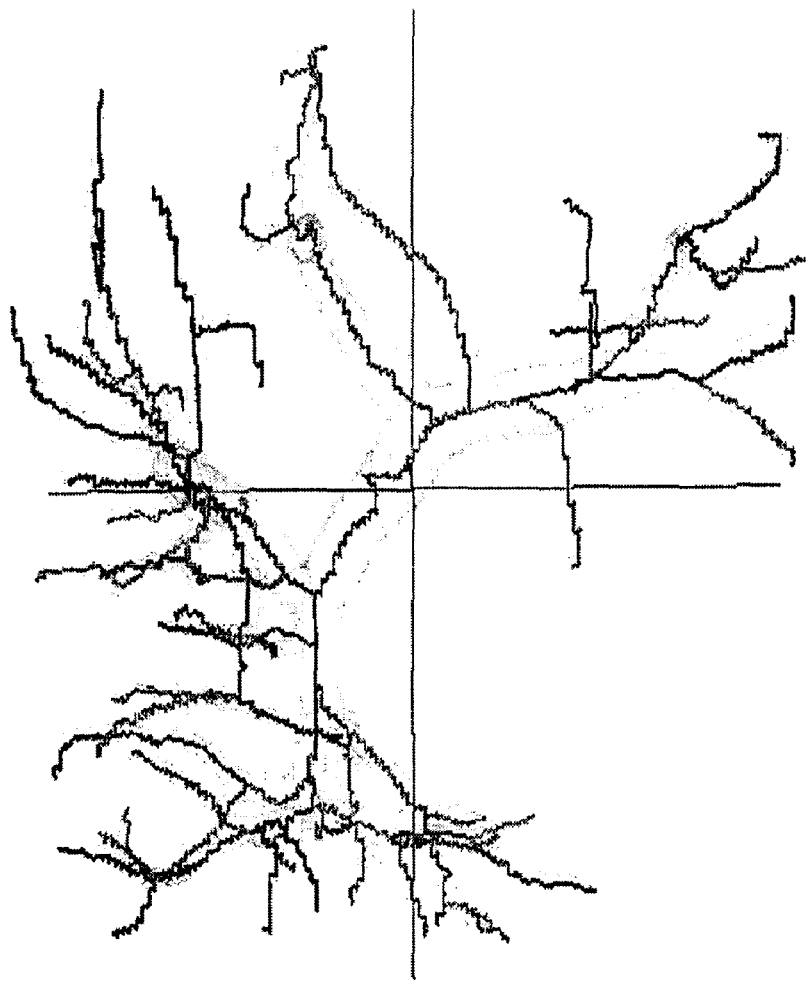
FIG. 2(b) provides an example of a skeleton representation of a three dimensional tubular structure.
Figure 2C:
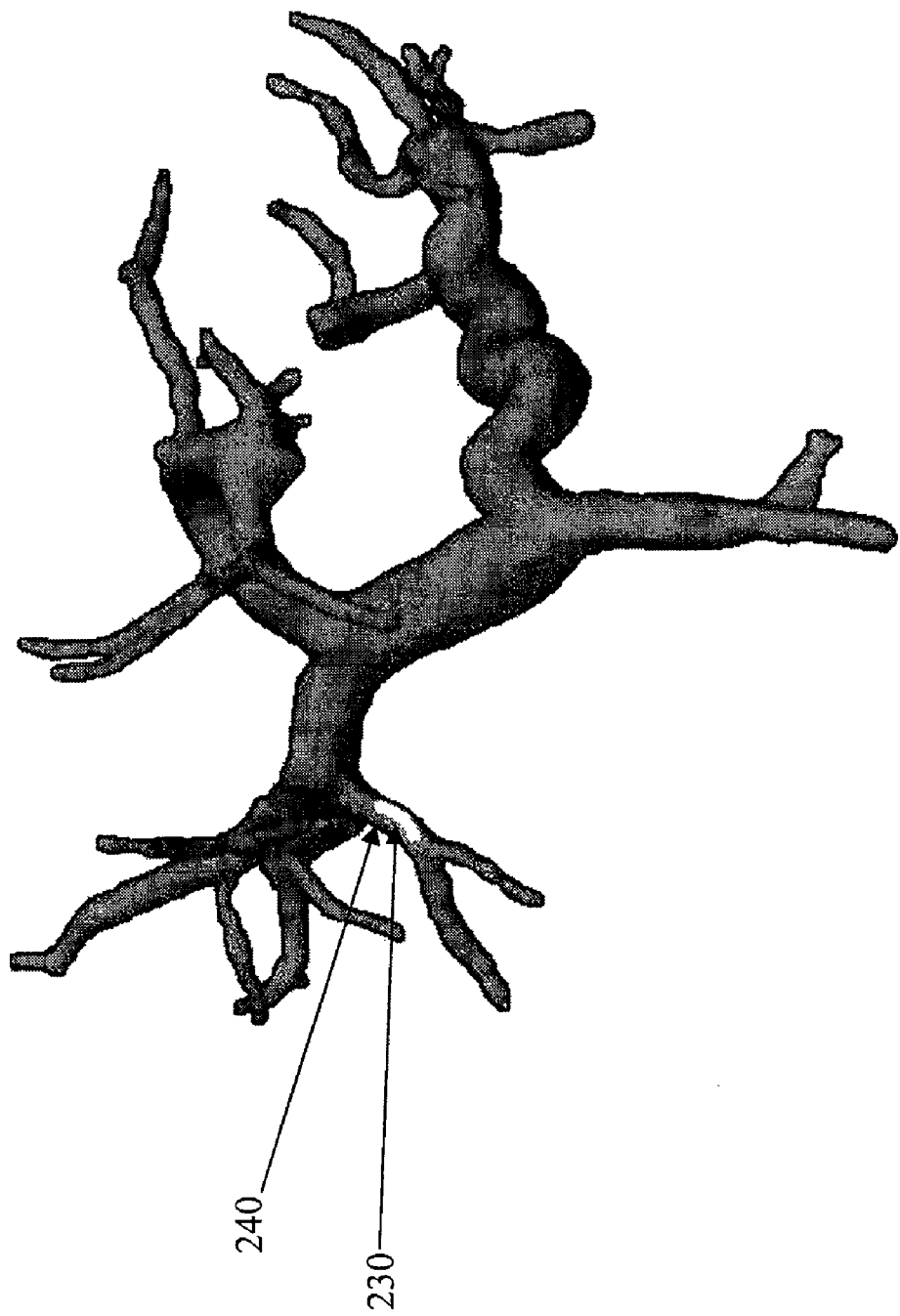
FIG. 2(c) illustrates a drawn line superimposed on a tubular segment that is made according to an embodiment of the present teaching.

Based on the drawn path 230 and the representation of the tubular structure, e.g., skeleton representation as shown in FIG. 2(b), the underlying tubular segment 240 that corresponds to the drawn path may be identified. To achieve that, the correspondence between the drawn line 230 and the representation (e.g., skeleton) of the tubular structure is first computed at 226. Then, based on such correspondence, tubular segments corresponding to the user drawn curve is also identified at 226. Details related to computation to identify such correspondence are discussed with reference to FIGS. 3-4(h). The label assigned to the drawn curve is then automatically assigned, at 228, to such identified tubular segment (s).

In some situations, a drawn curve may correspond to several tubular segments after the extension from the user-drawn curve. In some situations, such identified tubular segments may correspond to a sub-tubular structure. In some situations, different tubular segments so identified may correspond to broken tubular segment. In this case, those tubular segments corresponding to the same drawn curve are merged, at 230, into an integrated tubular segment so that the entire merged tubular segment is assigned the same label as the one associated with the drawing pen.

The above steps may be repeated until all desired branches of the tubular structure are labeled. The result of such operations corresponds to labeled segmented tubular structure 122 with desired branches labeled and broken segments connected. In addition, the order of the specific steps shown in FIG. 2(a) may vary. In some embodiments, a user may draw along a tubular segment first, the system then extracts corresponding pixels/voxels, and the user may then select a label and assign it to the extracted pixels/voxels.

As seen above, the labeling operation as described herein for labeling of a tubular structure may be used to correct or refine the tubular structure segmentation result. In some embodiments, the above steps may be performed on branch that has been labeled previously. In such cases, input to the system may be labeled tubular structures. A user may draw a path along a preferred tubular segment as if he/she is performing a labeling as described herein and then assign a desired label to each tubular segment corresponding to the drawn curve.

In another exemplary embodiment, a user may change all the segments having a prior assigned label to a different label. For example, a user may select a particular label to be changed and specify a new label to be used to replace the particular label. Correspondingly, all the segments having this particular label can be selected and replaced the new label.

Figure 1B:
FIG. 1(b) provides an example of a three dimensional tubular structure corresponding to a human vessel system.

In some embodiments, labels selectable from 106 (FIG. 1(a)) may include special labels that are in addition to the labels defined from, e.g. an anatomic atlas. Examples of such additional labels include a null label. Such a label may be given a special meaning to be used to indicate a special status of an underlying tubular segment. For instance, if a null label is selected and assigned to a tubular segment, it may indicate that the underlying tubular segment is to be deleted. This is especially useful when used in the context of spurious tubular segment(s) that are generated due to erroneous segmentation operation.

In some embodiment, the afore mentioned labeling process may be performed without having to segmenting out the tubular structures. For example, volume rendering techniques may be used to display a non-segmented tubular structure on the screen based on original images only. Furthermore, a skeleton representation may also be computed directly from original images.

Figure 3:
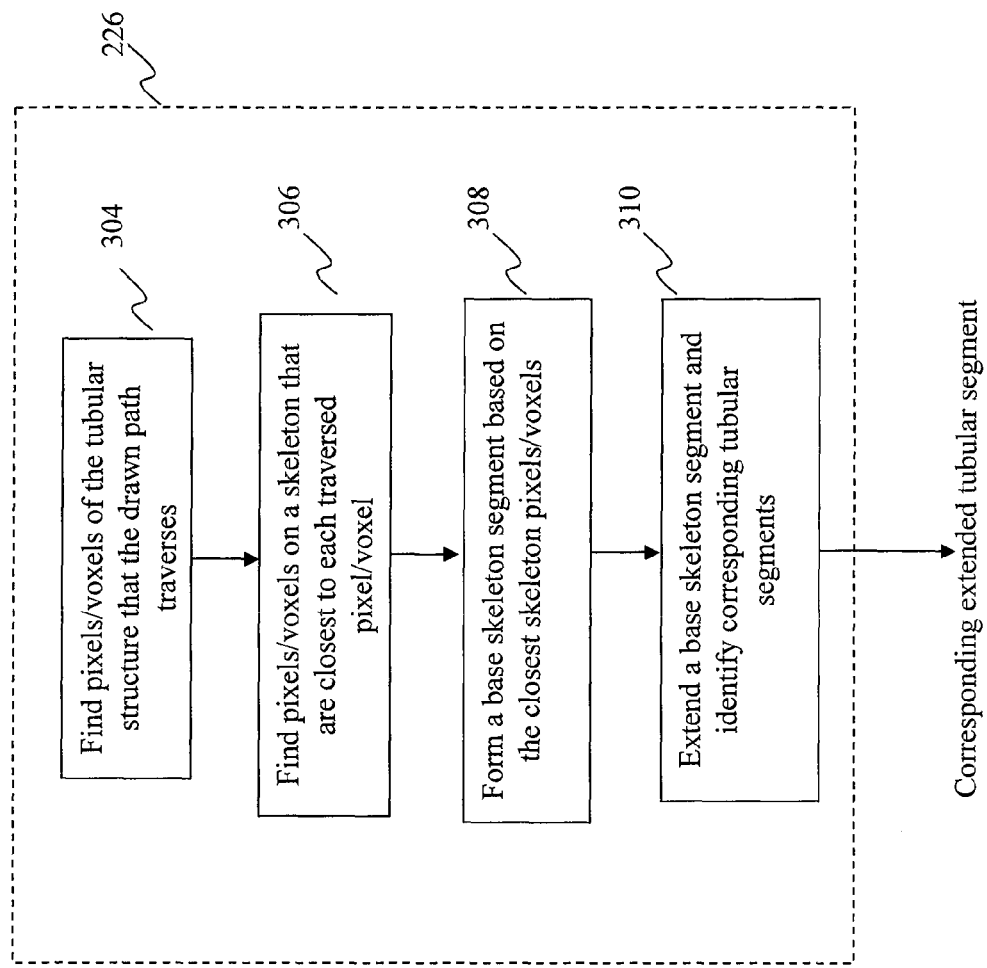
FIG. 3 is a flowchart of an exemplary process for computing a correspondence between a drawn path and a skeleton representation of a tubular structure, according to one embodiment of the present teaching.
Figure 4A:
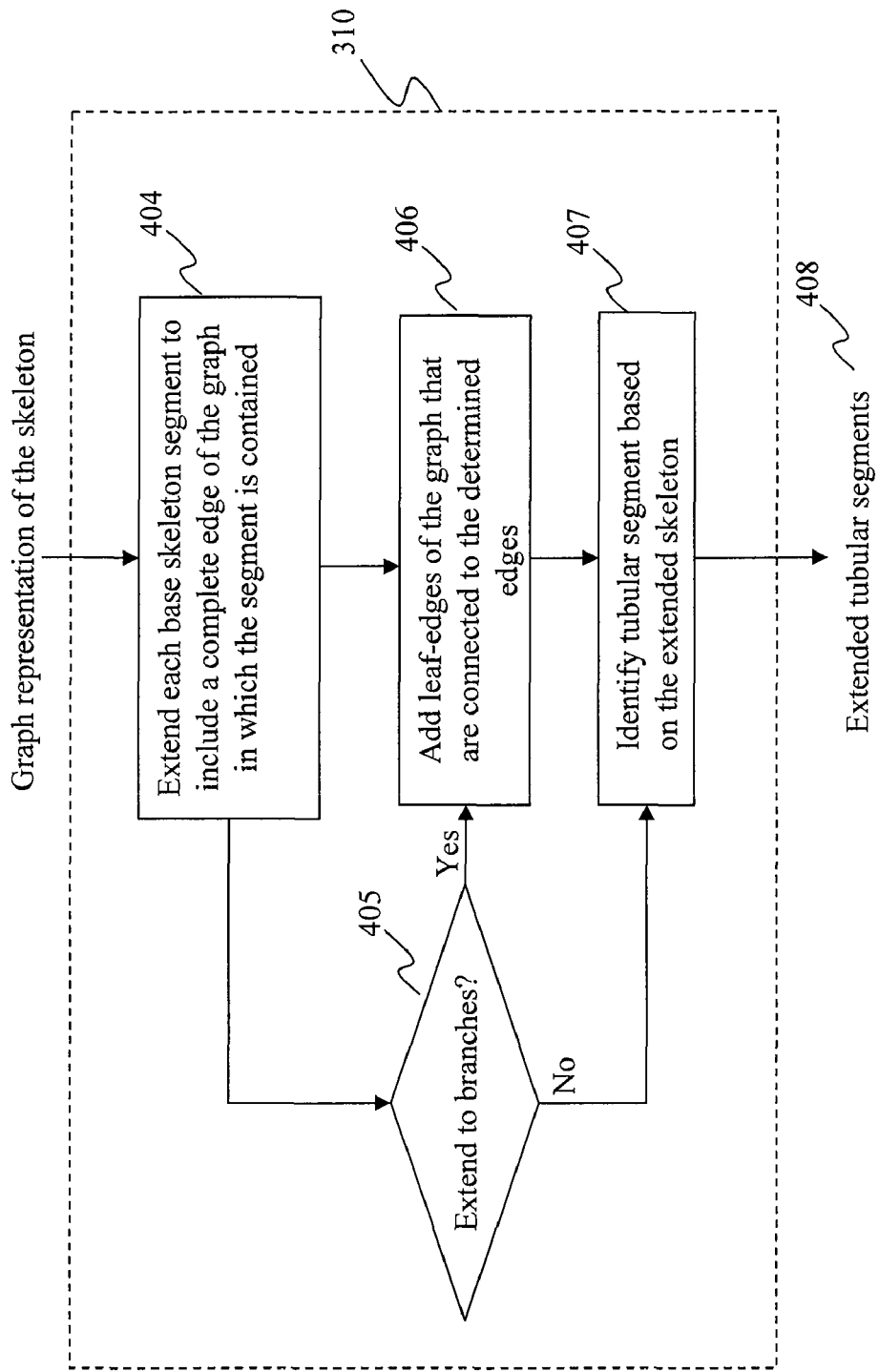
FIG. 4(a) is a flowchart of an exemplary process for extending a base skeleton, according to one embodiment of the present teaching.
Figure 4B:
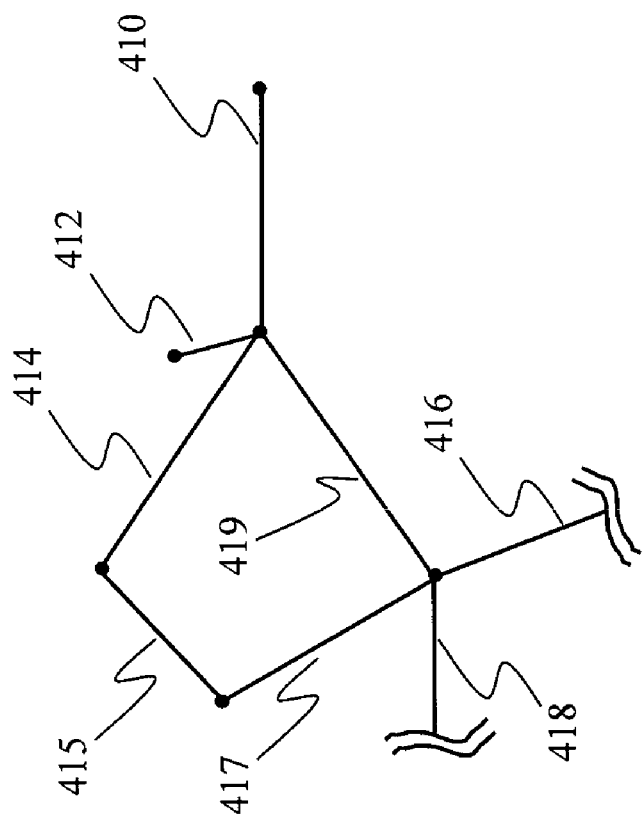
FIG. 4(b) illustrates an a graph representation of a skeleton, according to an embodiment of the present teaching.
Figure 4C:
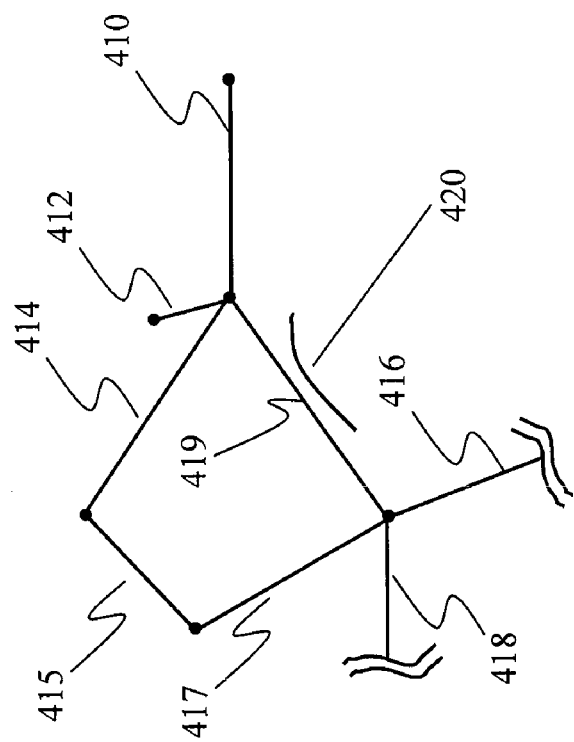
FIG. 4(c) illustrates an a graph representation of a skeleton, together with a drawn line, according to an embodiment of the present teaching.
Figure 4D:
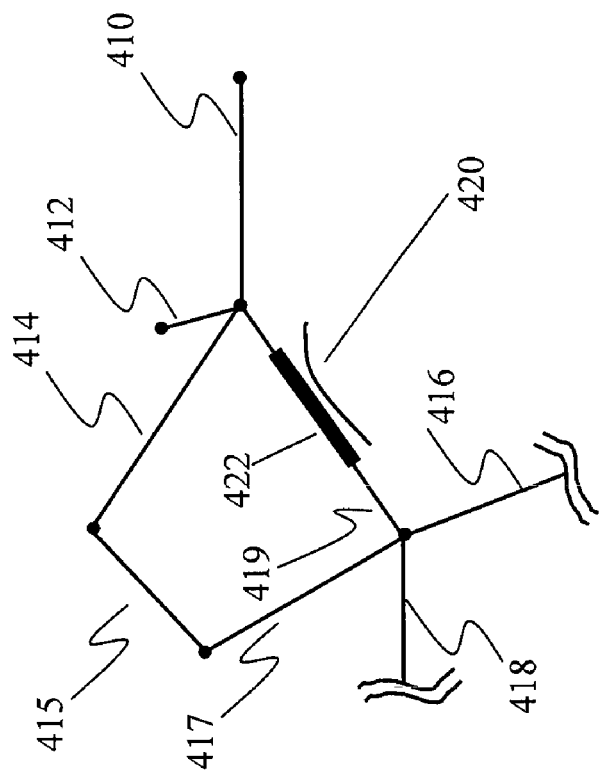
FIG. 4(d) illustrate the base skeleton segment corresponding to the drawn line, according to an embodiment of the present teaching.
Figure 4E:
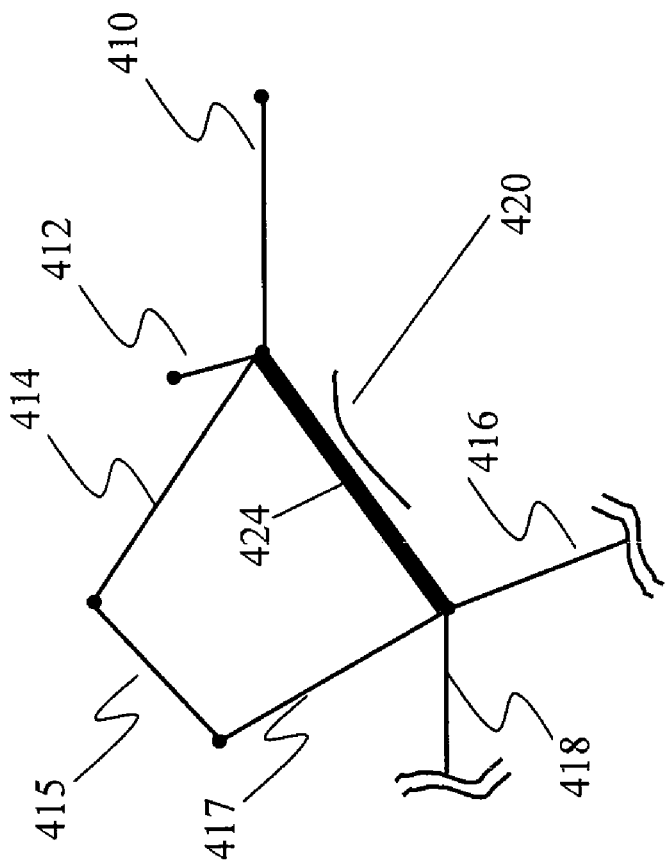
FIG. 4(e) illustrate the an extension of the base skeleton to include the entire skeleton segment, according to an embodiment of the present teaching.
Figure 4F:
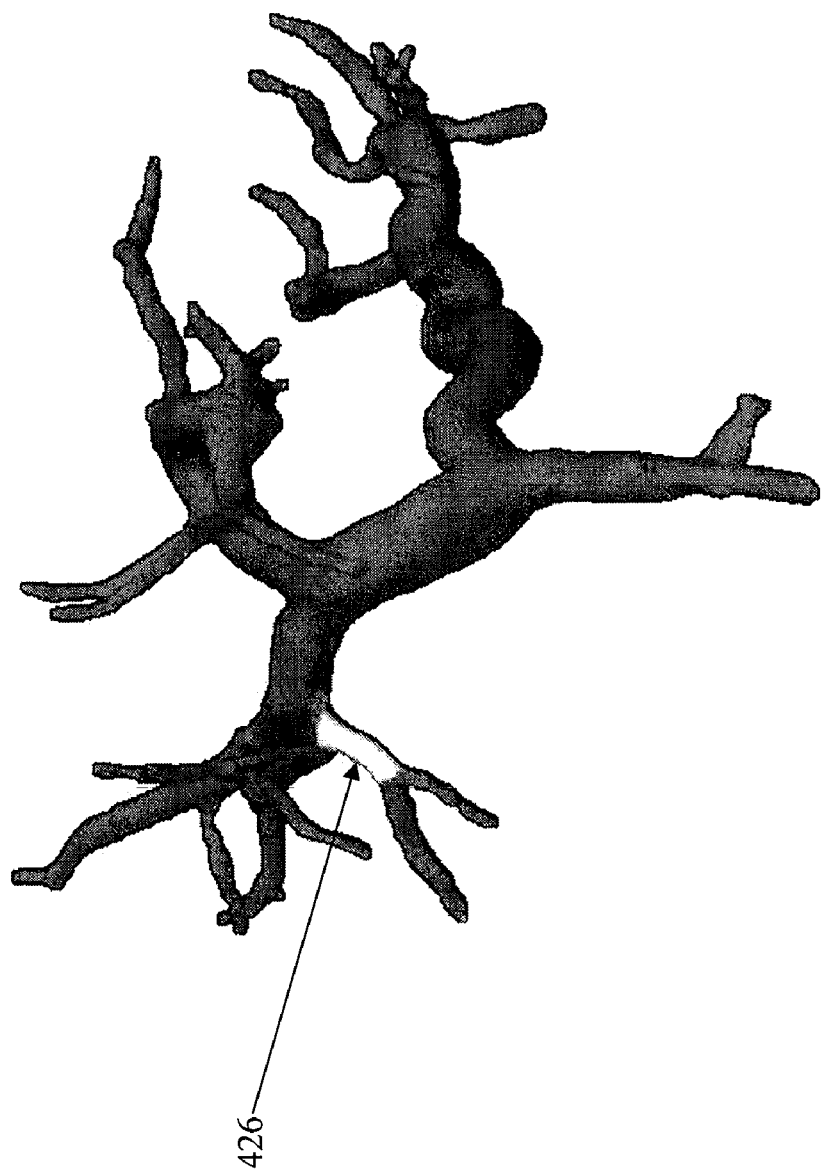
FIG. 4(f) illustrates an extended tubular segment derived based on a drawn line, according to an embodiment of the present teaching.
Figure 4G:
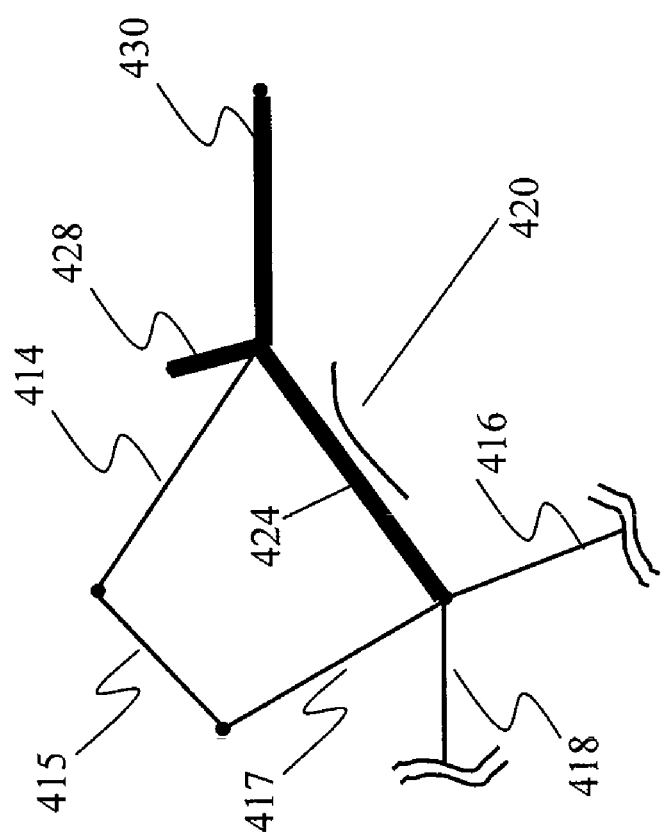
FIG. 4(g) illustrate an extension of the base segment to include non-circular sub-segments, according to an embodiment of the present teaching.
Figure 4H:
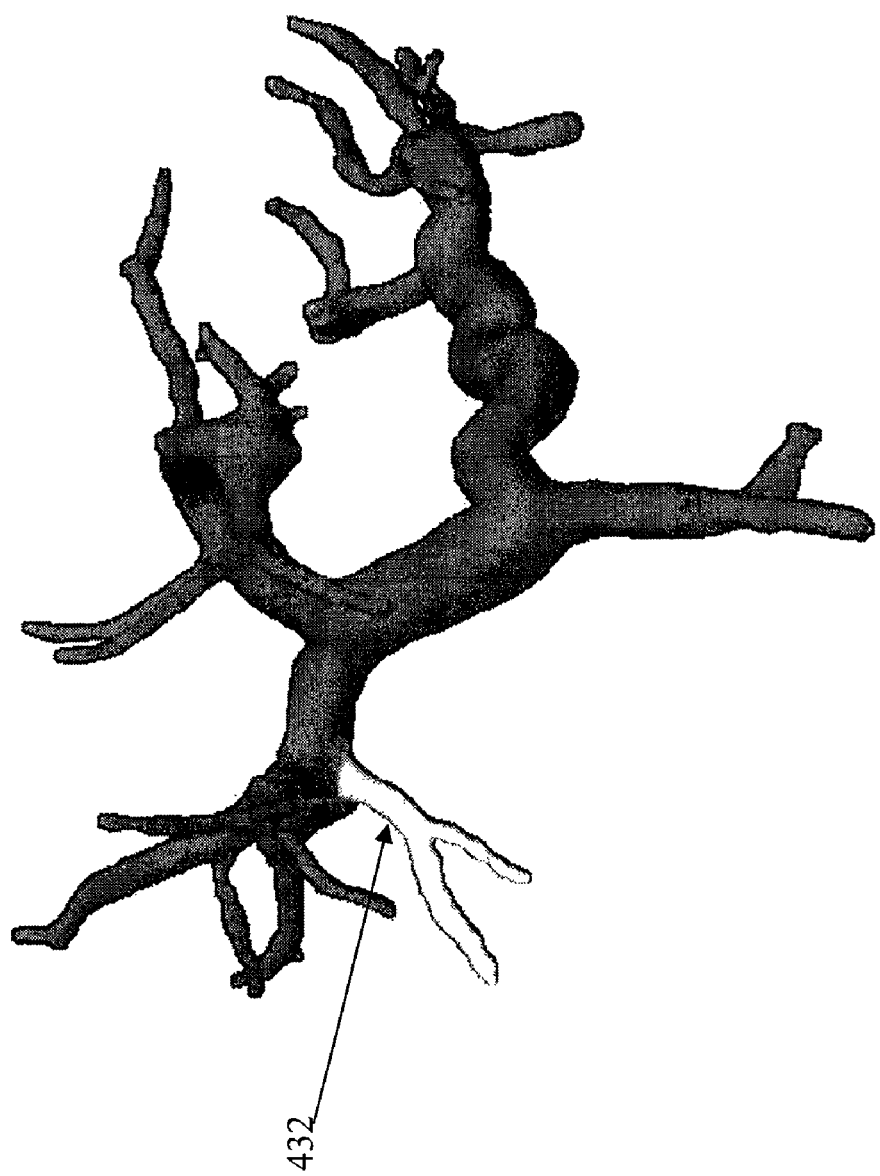
FIG. 4(h) illustrates another extended tubular segment derived based on a drawn line, according to an embodiment of the present teaching.

Details regarding how to identify corresponding tubular segment(s) (step 226 in FIG. 2(a)) is discussed in FIG. 3, which is a flowchart of an exemplary process in which a correspondence between a skeleton representation of tubular structures and a path drawn along a tubular segment is computed, according to an embodiment of the present teaching. To identify tubular segment(s) corresponding to a user drawn curve, a representation of the tubular structure such as a skeleton representation may be utilized. In some embodiments, the skeleton representation of a tubular structure comprises central lines of segmented tubular segments in the tubular structure. One example of such a skeleton of a tubular structure is shown in FIG. 2(b).

Pixels or voxels on the segmented tubular structure that the user drawn path traverses may first be identified at 304. For example, if the underlying tubular structure is a 3D structure, a pixel on the drawn path may map to a ray of voxels in the 3D space passing through the pixel along a viewing direction. The intersection of the ray with the tubular structure may then be identified as voxels that the user drawn path traverses. In another example, a user may use a 3D mouse and alike device to mark directly in the 3D space where the tubular structure is rendered. In this case, all points that are marked in the 3D space are treated as the points that the user drawn path traverses.

At step 306, for each of the pixels/voxels that the user drawn path traverses, the closest pixels/voxels on the skeleton representation of the tubular segments are identified. In some situations, such determined closest pixels/voxels in the skeleton representation of the tubular segments may not be connected due to, e.g., variations in the user-drawn paths. In addition, instead of identifying such closest points, other identifying approach may also be used. For instances, in the skeleton representation, there may be a plurality of skeleton segments. Some of the skeleton segments may be considered as close to the user drawn curve if their proximity measured in accordance with some kind of distance, e.g., Euclidian distance, to the user drawn curve or some points thereof, is within some pre-determined threshold.

At step 308, a base skeleton may be formed based on the closest pixels/voxels selected at 306. Although the closest pixels/voxels may not be continuously connected in the 2D or 3D space, they can be connected based on some criterion or extrapolation approach. The connection can be made manually, semi-automatically or automatically. The resulting connected skeleton forms a base skeleton segment. In actual operation, a user sometimes may not draw a curve that expands the whole length of a tubular segment, as seen in FIG. 2(c), where the user drawn curve 230 is shorter than the length of the underlying tubular segment 240. In this case, the base skeleton segment formed based on the closest pixels/voxels identified at 306 may not be corresponding well to the underlying tubular segment 240. Therefore, at 310, such formed base skeleton is extended so that it can more truthfully represent the underlying tubular segment 240.

There may be different modes of operation in terms of extending the base skeleton to more accurately identify the underlying tubular segment (240). In some embodiments, different operational modes may be provided as choices to a user so that the user may activate a mode of operation suitable to the underlying application. In one mode, the base skeleton may be extended to cover the length of the underlying tubular segment. In this case, the skeleton segment that has the most closest pixels/voxels, as identified at 306, may be used as the extended skeleton segment.

Details of step 310 may be implemented in accordance with the flowchart as shown in FIG. 4(*a*). In this implementation, a skeleton representation may be implemented based on a graph, in which each skeleton corresponding to two nodes and an edge in between. Such a graph may be constructed from the skeleton representation of a tubular structure and it includes nodes and edges linking different nodes. In a graph representing a skeleton representation, a node in the graph represents an intersection of two or more skeleton segments. An edge in the graph represents a skeleton segment connecting two nodes in the graph. A tree is defined as a set of edges stemming from one edge without loops in the edges.

The edge of each skeleton comprises a plurality of edge points. This is illustrated in FIG. 4(*b*), where there are a plurality of skeleton segments in a skeleton representation. For example, as illustrated there are skeleton segments 410, 412, 414, 415, 416, 417, 418, and 419. There are two nodes and one edge for each skeleton segment and some nodes may be connected to different edges, which are candidates for branches. Based on this implementation of the skeleton representation for a tubular structure, the operations as described in FIG. 4(*a*) can be carried out to extend a base skeleton to generate an extended skeleton.

In operation, to extend a base skeleton, the base skeleton is first extended, at 404, to recover the correct length of a tubular segment that corresponds directly to a user drawn curve. This is illustrated in FIGS. 4(*b*)-4(*d*). In FIG. 4(*b*), a skeleton representation of a part of a tubular structure is shown, in which different skeletons, 410, 412, 414, 415, 416, 417, 418, and 419 represent different segments of the tubular structure. In this example, skeletons 414, 415, and 417 form a loop, which in most situations may represent an error because physiologically, a vascular system usually does not have circular vessels.

In FIG. 4(*c*), a user drawn curve 420 is shown together with skeleton representation of the tubular structure as shown in FIG. 4(*b*). The user drawn curve 420 is in proximity to skeleton 419. After performing step 306, the pixels on a skeleton that are closest to the user drawn curve are likely all from skeleton 419 and they form a base skeleton according to step 308. This is shown in FIG. 4(*d*), where these closest skeleton points form a base skeleton 422. As can be seen, this base skeleton, although corresponding to an existing skeleton 419, does not have the same length as that of 419.

In extending the base skeleton to cover the entire length, at step 404 of FIG. 4(*a*), the edge points along the underlying existing skeleton (e.g., 419) is recovered as the extended skeleton 424, as shown in FIG. 4(*e*). In some mode of operation in accordance with the present teaching, a base skeleton is used to extend only to the underlying tubular segment without extending to the branches thereof. The mode of operation is determined at 405. If it is not to be extended to branches, the extended skeleton shown in FIG. 4(*e*) is used directly to identify a tubular segment that corresponds to the user drawn curve. In this example, the corresponding tubular segment 426 identified based on the extended skeleton 424 is shown in FIG. 4(*f*), which corresponds to the user drawn curve 230 as shown in FIG. 2(*c*).

In a different mode of operation, initial extended skeleton derived based on a base skeleton may expand further to some of the branches of the tubular segment 424. In this case, the operation at 406 is performed, which adds all branches of tubular segment 424 except branches that contain loops to the extended skeleton. In implementation, this corresponds to leaf edges, i.e., edges that have one node that is not connected to other edges, that are connected, directly or indirectly, to the tubular segment 424. The result is illustrated in FIGS. 4(*d*), 4(*e*), 4(*g*), and 4(*h*), where the base skeleton 422 may first be extended to skeleton segment 424 in FIG. 4(*e*). Then the extended skeleton segment 424 can be further extended to its branches, as shown in FIG. 4(*g*), where the extended skeleton segment 424 has branches 428 and 430, that are both corresponding to leaf-edges having one node connected to other edges. In some embodiments, all edges that are only connected to leaf edges may be included in the extension operation. For example, if segment 410 are connected 2 sub-segments, both segment 410 and the sub-segments may be included.

Such extension may be controlled according to some criteria. For example, the extension may be limited to only branches that physiologically are acceptable, e.g., a loop structure in the skeleton representation may not be included in such extension. In FIG. 4(*g*), although skeleton 414 is also a branch of 424, it is not accepted as an extension because from 414, there is a loop going to back the skeleton 424. Therefore, the extension performed in accordance with the second mode of operation (steps 404, 406, and 407) produces an extended skeleton as shown in FIG. 4(*h*), which includes skeleton segments 424, 428, and 430. Using the example tubular structure shown in FIG. 2(*c*) with a user drawn curve 230, the corresponding tubular segments identified using the process illustrated in FIG. 4(*a*) yields resulting tubular structure 432, shown in FIG. 4(*h*), corresponding to the user drawn curve 230.

Figure 5:
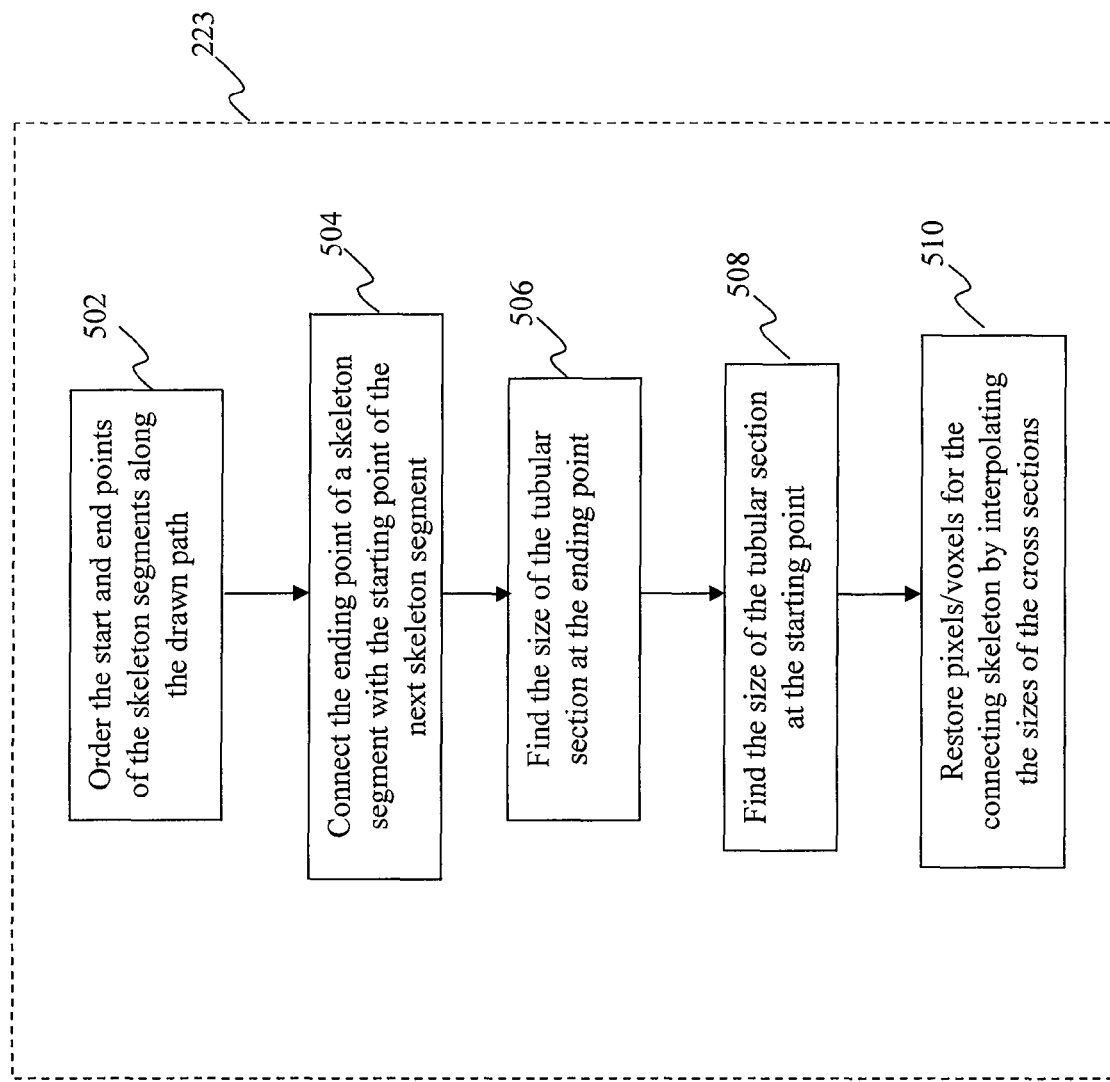
FIG. 5 is a flowchart of an exemplary process for connecting separate tubular structures along a drawn line, according to one embodiment of the present teaching.

FIG. 5 is a flowchart of an exemplary process in which broken tubular segments along a user drawn path are merged, according to one embodiment of the present teaching. At step 502, a plurality of skeleton segments along a user drawn path may be ordered in sequence along a given direction of the user drawn path. In implementation, this may be to arrange a series of starting and ending points from each of the skeleton segments in a sequence. At step 504, a new skeleton segment may be introduced between any two adjacent broken skeleton segments. The new skeleton segment may be generated based on the ordered multiple skeleton segments by connecting the ending point of a skeleton segment and the starting point of its adjacent skeleton segment. In this manner, the newly generated skeleton segment links the two broken skeleton segments.

Since the two broken skeleton segments may represent two tubular segments of different diameters, the new tubular segment represented by the newly generated skeleton segment needs to be generated in accordance with the widths of its neighboring tubular segments. At step 506, the diameter of the cross section of the tubular segment at the ending point of the previous tubular segment is computed. At step 508, the diameter of the cross section at the starting point of the next tubular segment is computed. Such computed diameters of the adjacent tubular segments are then used to construct the newly inserted tubular segment.

At step 510, interpolation is performed to generate cross sections between the cross-section corresponding to the ending point of the previous tubular segment and that corresponding to the starting point of the next tubular segment. Depending on the shape of the previous and next tubular segment, different interpolation schemes may be employed. For instance, if a straight tubular segment is inserted, a linear interpolation may be used to generate a straight tubular segment whose diameter may tape from one end to the other linearly based on the diameters of the neighboring tubular segments. If the newly generated tubular segment needs to be curved, a tubular segment with a curved shape may be used with its cross section diameter gradually change from one end to the other to smoothly connecting to the two neighboring tubular segments. In another exemplary embodiment, averaged sizes close to ending or starting points may be used for more robustness. In some embodiments, the precise shape of the newly generated tubular structure may be determined based on some optimization that is determined based on the intensity values of the pixels/voxels near the boundary of the new tubular structure.

While the inventions have been described with reference to the certain illustrated embodiments, the words that have been used herein are words of description, rather than words of limitation. Changes may be made, within the purview of the appended claims, without departing from the scope and spirit of the invention in its aspects. Although the inventions have been described herein with reference to particular structures, acts, and materials, the invention is not to be limited to the particulars disclosed, but rather can be embodied in a wide variety of forms, some of which may be quite different from those of the disclosed embodiments, and extends to all equivalent structures, acts, and, materials, such as are within the scope of the appended claims.

We claim:

1. A method for labeling a tubular structure on a display screen of a device, comprising steps of:
    displaying a tubular structure on a display screen;
    obtaining a representation of the tubular structure;
    displaying a curve on the display screen based on information received from a user who draws the curve on the display screen using an electronic pen associated with a label;
    identifying one or more segments of the tubular structure that corresponds to the drawn curve based on the representation of the segmented tubular structure; and
    assigning the label to the one or more segments of the tubular structure.

2. The method of claim 1, wherein the tubular structure is one of two dimensional and three dimensional.

3. The method of claim 1, wherein the display screen allows the tubular structure to be rendered in a two-dimensional space.

4. The method of claim 1, wherein the representation of the tubular structure is a skeleton representation.

5. The method of claim 1, wherein the label is represented as one of:
    a color;
    a textual anatomical description;
    an annotation;
    an identification; and
    a special marker encoded with a special instruction for an action.

6. The method of claim 5, wherein the special marker includes a NULL marking with an instruction for a deletion operation.

7. The method of claim 1, wherein the electronic pen has a tip of a certain size.

8. The method of claim 7, wherein the tip size is selectable.

9. The method of claim 7, wherein the tip size can be dynamically adjusted in accordance with the width of a tubular segment at the location of the tip.

10. The method of claim 7, wherein the electronic pen or the tip size can be manipulated by a user via an interactive interface.

11. The method of claim 1, wherein the step of identifying comprises:
    locating pixels/voxels of the tubular structure that the drawn curve traverses;
    locating, for each pixel/voxel the drawn curve traverses, one or more elements of the representation of the segmented tubular structure that are closest to the each pixel/voxel;
    generating a base skeleton segment based on the elements of the representation that are closest; and
    extending the base skeleton segment to identify the one or more tubular segments in the tubular structure.

12. The method of claim 11, wherein the step of extending the base skeleton segment comprises:
    obtaining a graph representation of a skeleton of the tubular structure, where each tubular segment of the tubular structure is represented based on a skeleton segment having an edge, representing the length of the tubular segment, and two nodes, representing two ends of the tubular segment;
    identifying a skeleton segment, which overlaps with the base skeleton segment, as the extended skeleton segment; and
    extracting a tubular segment from the segmented tubular structure represented by the extended skeleton segment as the tubular segment corresponding to the drawn curve.

13. The method of claim 11, wherein the step of extending the base skeleton segment comprises:
    obtaining a graph representation of a skeleton of the tubular structure, where each tubular segment of the tubular structure is represented based on a skeleton segment having an edge, representing the length of the tubular segment, and two nodes, representing two ends of the tubular segment;
    identifying a skeleton segment, which overlaps with the base skeleton segment, as the extended skeleton segment;
    tracing one or more branches, if any, of the extended skeleton segment that are non-circular; and
    extracting the one or more tubular segments represented by the extended skeleton segment and its non-circular branches as the tubular segments corresponding to the drawn curve.

14. The method of claim 1, further comprising:
    merging at least some of the one or more tubular segments that are not connected;
    generating a merged tubular segment; and
    assigning the label to the merged tubular segment.

15. The method of claim 14, wherein the step of generating comprises:
    ordering start and ending points of skeleton segments identified along the drawn curve;
    connecting an ending point of a skeleton segment with a starting point of a next skeleton segment;
    obtaining first diameter information at the ending point of a first tubular segment corresponding to the skeleton segment;
    obtaining second diameter information at the starting point of a second tubular segment corresponding to the next skeleton segment; and
    interpolating a new tubular segment between the first and second tubular segments based on the first diameter and second diameter information.

16. A system for labeling a tubular structure on a display screen of a device, comprising:
    a display device having a display screen;

a display unit configured for displaying a tubular structure on a display screen;

a tubular structure representation generation unit configured for obtaining a representation of the tubular structure;

an interactive drawings unit configured for enabling a user to draw a curve on the display screen using an electronic pen associated with a label;

a tubular segment extraction unit configured for identifying one or more segments of the tubular structure that corresponds to the drawn curve based on the representation of the segmented tubular structure; and a label assignment unit configured for assigning the selected label to the one or more segments of the tubular structure.

17. The system of claim 16, wherein the tubular structure is one of two dimensional and three dimensional.

18. The system of claim 16, wherein the display screen allows the tubular structure to be rendered in a two-dimensional space.

19. The system of claim 16, wherein the representation of the tubular structure is a skeleton representation.

20. The system of claim 16, wherein the label is represented as one of:
   a color;
   a textual anatomical description;
   an annotation;
   an identification; and
   a special marker encoded with a special instruction for an action.

21. The system of claim 20, wherein the special marker includes a NULL marking with an instruction for an deletion operation.

22. The system of claim 16, wherein the electronic pen has a tip of a certain size.

23. The system of claim 22, wherein the tip size is selectable.

24. The system of claim 22, wherein the tip size can be dynamically adjusted in accordance with the width of a tubular segment at the location of the tip.

25. The system of claim 22, wherein the electronic pen or the tip size can be manipulated by the user via an interactive interface.

26. The system of claim 16, further comprising a correspondence computation unit configure for identifying correspondences between the drawn curve and the one or more tubular segments, wherein the correspondence computation unit is capable of:
   locating pixels/voxels of the tubular structure that the drawn curve traverses;
   locating, for each pixel/voxel the drawn curve traverses, one or more elements of the representation of the segmented tubular structure that are closest to the each pixel/voxel;
   generating a base skeleton segment based on the elements of the representation that are closest; and
   extending the base skeleton segment to identify the one or more tubular segments in the tubular structure.

27. The system of claim 26, wherein the extending the base skeleton segment comprises:
   obtaining a graph representation of a skeleton of the tubular structure, where each tubular segment of the tubular structure is represented based on a skeleton segment having an edge, representing the length of the tubular segment, and two nodes, representing two ends of the tubular segment;
   identifying a skeleton segment, which overlaps with the base skeleton segment, as the extended skeleton segment; and
   extracting a tubular segment from the segmented tubular structure represented by the extended skeleton segment as the tubular segment corresponding to the drawn curve.

28. The system of claim 26, wherein the extending the base skeleton segment comprises:
   obtaining a graph representation of a skeleton of the tubular structure, where each tubular segment of the tubular structure is represented based on a skeleton segment having an edge, representing the length of the tubular segment, and two nodes, representing two ends of the tubular segment;
   identifying a skeleton segment, which overlaps with the base skeleton segment, as the extended skeleton segment;
   tracing one or more branches, if any, of the extended skeleton segment that are non-circular; and
   extracting the one or more tubular segments represented by the extended skeleton segment and its non-circular branches as the tubular segments corresponding to the drawn curve.

29. The system of claim 16, further comprising a merging unit capable of:
   merging at least some of the tubular segments that are not connected;
   generating a merged tubular segment; and
   assigning the selected label to the merged tubular segment.

30. The system of claim 29, wherein the step of generating comprises:
   ordering start and ending points of skeleton segments identified along the drawn curve;
   connecting an ending point of a skeleton segment with a starting point of a next skeleton segment;
   obtaining first diameter information at the ending point of a first tubular segment corresponding to the skeleton segment;
   obtaining second diameter information at the starting point of a second tubular segment corresponding to the next skeleton segment; and
   interpolating a new tubular segment between the first and second tubular segments based on the first diameter and second diameter information.

* * * * *